United States Patent [19] [11] 4,271,088
Butte, Jr. et al. [45] * Jun. 2, 1981

[54] HIGH SELECTIVITY CYANOALKYLATION PROCESS

[75] Inventors: Walter A. Butte, Jr., West Chester; Wesley R. Cherry, Prospect Park, both of Pa.

[73] Assignee: Suntech, Inc., Philadelphia, Pa.

[*] Notice: The portion of the term of this patent subsequent to Oct. 16, 1996, has been disclaimed.

[21] Appl. No.: 40,248

[22] Filed: May 18, 1979

Related U.S. Application Data

[63] Continuation-in-part of Ser. No. 916,394, Jun. 16, 1978, Pat. No. 4,171,322.

[51] Int. Cl.³ .......................................... C07C 120/00
[52] U.S. Cl. .................... 260/465.6; 260/464; 260/465 R; 260/465 D; 260/465 E; 260/465 F; 260/465.1; 260/465.4; 260/465.5 R
[58] Field of Search .......... 260/465.6, 465.1, 465.8 R, 260/465.5 R, 465 F, 465.4, 465 D, 465 E, 464

[56] References Cited

U.S. PATENT DOCUMENTS

| | | | |
|---|---|---|---|
| 2,383,444 | 8/1945 | Bruson | 260/465.4 X |
| 2,386,736 | 10/1945 | Bruson | 260/465.1 |
| 2,394,962 | 2/1946 | Bruson | 260/465.8 R |
| 2,396,626 | 3/1946 | Wiest et al. | 260/465.4 |
| 2,437,905 | 3/1948 | Bruson | 260/465.6 |
| 2,460,536 | 2/1949 | Rogers | 260/465.1 X |
| 2,461,842 | 2/1949 | Olin | 260/465.4 |
| 2,547,686 | 4/1951 | Brockway | 260/465.8 R |
| 2,553,737 | 5/1951 | Albertson et al. | 260/465.4 |
| 2,579,580 | 12/1951 | Howk et al. | 260/465.1 |
| 2,816,130 | 12/1957 | Selcer et al. | 260/465.6 |
| 2,836,613 | 5/1958 | Heininger | 260/465.6 |
| 2,853,510 | 9/1958 | Montagna et al. | 260/465.6 |
| 3,024,267 | 3/1962 | Howsmon, Jr. | 260/465.6 |
| 3,150,142 | 9/1964 | Eby | 260/464 X |
| 3,151,150 | 9/1964 | Kamlet et al. | 260/465.6 X |
| 3,324,164 | 6/1967 | Merkel et al. | 260/465.6 X |
| 3,701,802 | 10/1972 | Maerker et al. | 260/465.6 X |
| 3,957,848 | 5/1976 | Reedy et al. | 260/465.6 |

FOREIGN PATENT DOCUMENTS

| | | |
|---|---|---|
| 990973 | 5/1965 | United Kingdom . |
| 1021319 | 3/1966 | United Kingdom . |
| 1045505 | 10/1966 | United Kingdom . |
| 1233089 | 5/1971 | United Kingdom . |
| 1309475 | 3/1973 | United Kingdom . |

OTHER PUBLICATIONS

Cyanoethylation; Kirk–Othmer, Encyclopedia of Chemical Technology; 2nd ed., vol. 6, 1965, pp. 634–664.
Bruson; Org. Reactions; vol. 5, 1949, pp. 79–113.
Chen; J. Org. Chem., 27, (1962), pp. 1920–1921.

Primary Examiner—Joseph Paul Brust
Attorney, Agent, or Firm—J. Edward Hess; Donald R. Johnson; Anthony Potts, Jr.

[57] ABSTRACT

In a cyanoalkylation process involving the reaction of a cyanoalkene compound such as acrylonitrile with a compound containing a labile hydrogen such as ethylene glycol, to form a cyanoalkylated product such as 3,3'-ethylenedioxybis(propionitrile), the conversion of the cyanoalkene is limited to about 60 to 96%, preferably 70 to 85%, whereby the formation of byproducts is reduced from that which is obtained when the conversion of the cyanoalkene is greater than about 96%.

10 Claims, 1 Drawing Figure

U.S. Patent   Jun. 2, 1981   4,271,088
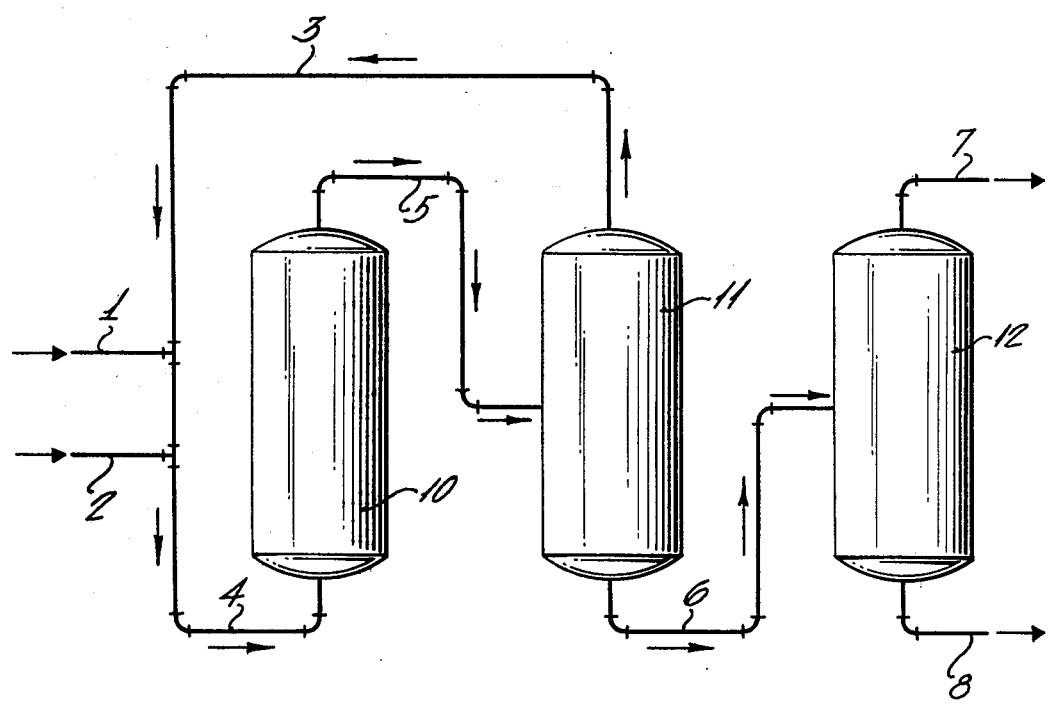

HIGH SELECTIVITY CYANOALKYLATION PROCESS

CROSS REFERENCE TO RELATED APPLICATION

This application is a continuation-in-part of U.S. patent application Ser. No. 916,394 filed June 16, 1978, now U.S. Pat. No. 4,171,322, issued Oct. 16, 1979, by the above-identified applicants.

BACKGROUND OF THE INVENTION

This invention is directed to an improvement in cyanoethylation and other cyanoalkylation processes. The process involved is preferably continuous, although it may also be performed in batch operations. The invention will be further described with reference to cyanoethylation processes, but it is understood that the invention is also useful in connection with other cyanoalkylation processes as further disclosed herein. The improvement of the invention involves limiting the conversion of the cyanoalkylating agent in order to avoid the formation of unwanted byproducts and improve the selectivity for the desired products.

Cyanoethylation refers to the reaction between acrylonitrile and a variety of compounds to yield β-substituted propionitrile derivatives. The compounds are characterized by their possession of a labile hydrogen atom. The latter is a hydrogen atom bonded to an electronegative atom or to an atom activated by strongly electronegative substituents. Classes of compounds containing labile hydrogen atoms include those having hydroxyl groups, e.g., polyhydric alcohols. Cyanoethylation can be generalized by the following reaction formula:

$$CH_2=CHCN + RH \rightleftharpoons RCH_2CH_2CN$$

For polyhydric alcohols the general reaction formulas are as follows:

$$CH_2=CHCN + HOROH \rightleftharpoons CNCH_2CH_2OROH$$

$$CH_2=CHCN + CNCH_2CH_2OROH \rightleftharpoons CNCH_2CH_2OROCH_2CH_2CN$$

Cyanoethylation products are useful intermediates for the manufacture of plastics and fibers.

Cyanoethylation is used in the formation of a great variety of polyfunctional nitriles, for example, see *Encyclopedia of Chemical Technology*, Kirk-Othmer, 2nd Edition, Volume 6, and *Organic Reactions*, R. Adams et al, Volume 5, John Wiley and Sons, New York 1949. Cyanoethylation using ion exchange resin catalyst is disclosed in *J. of Org. Chem.*, Vol. 27, May 1962, pages 1920–1921, "Catalysis by Ion Exchange Resins. Improved Cyanoethylation and Carbamylethylation of Diols".

The cyanoethylation reaction has a tendency to be accompanied by polymerization of the acrylonitrile. It is desirable to avoid the polymerization side reaction since valuable starting material is converted to less valuable byproducts. Techniques suggested to minimize the unwanted polymerization include maintaining a lower temperature by cooling the exothermic reaction, diluting the reaction mixture with an inert solvent, use of soluble or highly dispersed catalyst and the gradual addition of acrylonitrile with mechanical mixing. However, the aforementioned solutions suffered from various shortcomings such as additional capital expenditures, and/or additional materials handling costs, and/or additional separation steps and costs.

In U.S. Pat. No. 2,853,510, a soluble catalyst, a large excess of glycol over acrylonitrile, and gradual addition of acrylonitrile over 8 hours are employed in cyanoethylation of diethylene glycol (Example 4) to obtain 100% conversion of acrylonitrile to cyanoethylethers. Other ways of avoiding undesired byproducts are not suggested. Nor it is suggested that it would ever be desirable to operate at less than 100% conversion of acrylonitrile.

In U.S. Pat. No. 3,324,164, a soluble catalyst and intense mixing are employed in cyanoethylation of methanol (Embodiment I) with stoichiometric proportions of acrylonitrile and methanol, to obtain β-cyanoethyl methyl ether in 99% purity and amount equivalent to a yield of 98% of theory. Again other ways of avoiding undesired byproducts are not suggested, nor is it suggested that it would ever be desirable to operate at less than nearly complete conversion of acrylonitrile.

In U.S. Pat. No. 3,701,802, cyanoethylation of methyl-12-hydroxystearate for example is carried out in batch operation using excess acrylonitrile as solvent for the reaction. In obtaining cyanoethylation to the degree of 76.7% (Table II), relatively very large amounts of acrylonitrile polymer are formed, i.e., 0.4 gram of polymer per 0.5 gram of methyl-12-hydroxystearate. This indicates a total conversion of acrylonitrile well in excess of the stoichiometric amount for reaction with all the methyl-12-hydroxystearate. No practical way is suggested for overcoming the problem of excessive formation of unwanted product while still obtaining a satisfactory degree of cyanoethylation.

Other cyanoalkylation processes are disclosed in U.S. Pat. Nos. 2,280,790; 2,404,164; 2,579,580; 2,836,613; 2,853,510; 3,024,267; 3,150,142; 3,151,150 and 3,957,848. Various degrees of conversion of the compound which is cyanoalkylated are disclosed, but such conversion is distinct from the degree of total conversion of the cyanoalkylating agent, which may undergo polymerization as well as cyanoalkylation reactions. These references do not suggest the importance of limiting the total conversion of the cyanoalkylating agent.

The process of the invention overcomes the aforementioned problem of an unwanted side reaction and avoids the shortcomings of the aforementioned solutions to the problem. By limiting the total conversion of cyanoalkylating agent, as set forth hereinafter, the process of the invention permits obtaining high selectivity for the desired cyanoethylation product, for example 3,3'-ethylene dioxybis(propionitrile) from the reaction between ethylene glycol and acrylonitrile, while the amount of acrylonitrile polymer formed is minimized. Further when certain reactants are used, as disclosed hereinafter, a product intermediate can be recycled and serves as a solvent and facilitates the reaction. Still further the resulting cyanoethylated product stream is of high purity which simplifies subsequent processing.

SUMMARY OF THE INVENTION

According to present invention, the conversion of the reaction between a cyanoalkene and a compound containing a labile hydrogen to form a cyanoalkylated product is limited to not more than about 96% whereby the formation of byproducts, e.g., polymer of the cyanoalkene, is reduced from that which is obtained when the conversion of the cyanoalkene is greater than about 96%. In a preferred embodiment the unreacted cyanoalkene, and any reaction intermediate is separated from the removed reaction mixture and recycled to the reaction zone.

BRIEF DESCRIPTION OF THE DRAWING

The accompanying FIGURE is a schematic drawing of one embodiment of the improved cyanoalkylation process.

EMBODIMENTS

In the FIGURE the cyanoalkene e.g., acrylonitrile 1 and the compound containing the labile hydrogen 2, e.g. the polyhydric alcohol, are admixed with recycle 3. The resulting mixture 4 consisting of acrylonitrile 1, a compound containing the labile hydrogen 2 and recycle 3 is introduced to reaction means 10. An inert solvent is optional. Reaction means 10 contains, e.g., a bed of basic ion exchange resin catalyst. Present in the reaction means 10 can be heat removal means (not shown). The reaction mixture 5 is removed from the reaction means 10 when the conversion of the acrylonitrile is between the range of from about 60% to about 96%. The reaction mixture 5 is forwarded to separation means 11, generally a distillation tower. The unreacted acrylonitrile, any reaction intermediate, which in the case of the reaction between acrylonitrile and ethylene glycol is 3-hydroxyethyleneoxypropionitrile, are separated and are recycled as recycle 3 back to reaction means 10. The bottoms 6 from separation means 11 is forwarded to separation means 12, generally a distillation tower. In separation means 12 the desired product 7 is separated from unwanted polymers and other unwanted by-products, if any, 8. Stream 8 can be further processed or disposed of in a suitable fashion. The product 7, which is essentially the cyanoethylated product, can be processed further and converted into useful plastics and fibers. The temperature of streams 3, 5, 6, 7 and 8 can be controlled by optional heat removal means (not shown).

Reaction means 10 is designed to provide a residence time, when considering feed and recycle rates, amount of catalyst contained therein, the amount of reactant products, and inert solvent, if used, and withdrawal rates so that the desired conversion results. Reaction means can be considered in terms of a batch or continuous reactor. The residence time can range between from about a quarter of an hour to about three to five hours or longer. Another way of indicating residence time is the amount of conversion that occurs. Conversion as used herein refers to the amount of e.g., acrylonitrile feed reacted to both desired and undesired products. The conversion by this improvement is limited to about 96% with about 85% preferred. If too low a conversion is used then the amount of separation and recycling becomes substantial and the overall result is a less efficient process. Thus the conversion is preferably in excess of at least about 60% with about 70% more preferred.

Termination of the reaction at the conversion levels specified herein is typically accomplished, in the case of a solid catalyst, by removing the reaction mixture from the catalyst bed, and in the case of a soluble liquid catalyst, by removing the catalyst from the reaction mixture by adsorption and/or neutralization of the catalyst, as by passage through a bed of acidic solid material. In general, termination of the reaction is accomplished by changing the conditions or by removing the catalyst so that substantial reaction no longer takes place.

Because the conversion is limited, recycle may be desirable, in order to avoid uneconomical raw material costs. Thus a recycle can consist of, in the case of where the other reactants are ethylene glycol and acrylonitrile, a monoadduct and some other materials including minor amounts of the desired diadduct. (If the other reactant contains three hydroxyls then a monoadduct and a diadduct are recycled). Recycling of the monoadduct permits it to react to form the desired diadduct thereby reducing raw material costs. In addition, the recycling of the monoadduct can replace the use of a solvent which helps lower costs. The amount of recycle can vary substantially. Generally, as a guide the amount of recycle can be in the range from about 10 wt.% to about 40 wt.% of the feed, i.e., polyhydric alcohol and acrylonitrile. A preferred amount of recycle is in the range from about 20 wt.% to about 30 wt.%.

As a result of limiting the conversion the selectivity is greatly enhanced. This is discussed further and data is provided under Examples. A result of the enhanced selectivity is that the amount of polymerization of acrylonitrile is substantially reduced and thus a selectivity in excess of about 95% is obtained and under more closely controlled conditions a selectivity of about 98% or higher can be obtained. Because of the high selectivity, the resulting product consists essentially of a cyanoethylated product and further purification is substantially reduced, if not eliminated completely. This is another advantage of limiting conversion as disclosed herein. Selectivity, as used herein, is defined as the percent of the acrylonitrile reacted to form a useful product which includes an intermediate which can further form the desired product.

The catalyst within reaction means 10 can vary. Various cyanoalkylation catalysts are known, for example see Kirk-Othmer, *Encyclopedia of Chemical Technology*, Volume 6, 2nd Edition, pages 634 and 635. The catalyst can be a liquid or solid or a combination thereof. Solid catalyst may be used in a fixed bed or fluid bed. Examples of a liquid catalyst include an aqueous sodium hydroxide while examples of a solid includes an ion exchange resin. The reaction also can be carried out non-catalytically. Several reactors can be used in series or in parallel.

The temperature of the reaction is maintained within the cyanoethylation reaction temperature range. Generally, as a guide the temperature can be in the range between from about 0° C. to about 100° C. If the temperature is too low the reaction rate will be too slow to be economical, whereas if it is too high, too much unwanted polymerization will occur and/or catalyst deactivation could be too rapid. A preferred temperature range is between from about 10° C. to about 90° C. with a range between about 30° C. to about 50° C. more preferred.

The mol ratio of cyanoalkylating agent to material to be cyanoalkylated may be varied as known in the art for cyanoalkylation processes. In one embodiment, the amount of cyanoalkylating agent is not greater than the stoichiometric amount for conversion of the material to be cyanoalkylated. Usually, the amount will be within 50%, preferably within 20%, of the stoichiometric amount for conversion to fully cyanoalkylated product.

Use of an inert solvent in the cyanoethylation process is optional. If the reactants are not completely miscible a mutual solvent can advantageously serve to insure the proper stoichiometry in reaction means 10. If an inert solvent is used, the amount would be equivalent to about 20-30 weight % of the fresh feed (excluding recycle). The solvent would be a low molecular weight, non-reactive solvent, preferably boiling under about 200° C. Ethers, particularly cyclic ethers, are suitable, e.g., p-dioxane and tetrahydrofuran.

As stated before, the catalyst may be a basic ion exchange resin. Such catalysts and variations thereof, are well-known and are described in the literature, e.g., *Encyclopedia of Chemical Technology*, 2nd Edition, Kirk-Othmer; Vol. 11, Ion Exchange. The amount of such catalyst used in reaction means 10 depends on many variables, e.g., volume of the reaction means 10, feed rate, amount of recycle and other such variables. Life of the catalyst depends on several variables such as reaction temperature and flow rates.

As mentioned heretofore, one of the reactants is characterized as an organic compound having a labile hydrogen atom. Typical such compounds which are known to undergo the cyanoethylation reaction include compounds having one or more —NH— groups, such as primary and secondary amines, lactams, amides; compounds having one or more —OH or —SH, groups such as monohydric or polyhydric alcohols (e.g., ethylene glycol, diethylene glycol, propylene glycol, 1,4-butylene glycol, 1,2-cyclohexane diol), phenols, mercaptans; —CH—, —CH$_2$— or —CH$_3$ group contiguous to the carbonyl groups; compounds having a methylene group activated by various radicals such as —CN (e.g., benzyl cyanide), —NO$_2$ (e.g., nitropropane), —COOH or —COOR (e.g., malonic esters); the ethylenic carbons of a carbocycle or heterocycle (e.g., cyclopentadiene, indene); and the like. Any organic compound susceptible of undergoing cyanoethylation may be used in the process of this invention.

While the previous discussion has referred to the use of acrylonitrile other agents having the structure CH$_2$=C(R)CN wherein R is a C$_1$-C$_5$ hydrocarbon radical are useable, e.g., alpha-methylacrylonitrile crotononitrile and beta-vinylacrylonitrile.

In related U.S. Application Ser. No. 916,393, filed June 16, 1978, now abandoned, by the present inventors, a process for cyanoalkylation without excessive formation of unwanted products is disclosed in which the cyanoalkylation reaction is carried out in the presence of cyanoalkylated product in addition to the cyanoalkylated product which is formed in situ by the reaction of the reactants.

The following examples illustrate the invention:

EXAMPLE

Generally the reaction of ethylene glycol and acrylonitrile was carried out in a 0.5 inch stainless steel jacketed column packed with 20 g. of basic ion exchange resin (Amberlyst A-26, Rohm & Hass). The resin was activated by washing it with 40 ml. of 10% caustic and washing with distilled water until the effluent was neutral to phenolphthalein.

A solution of 310 g. (5 moles) ethylene glycol and 530 g. (10 moles) acrylonitrile in 500 g. dioxane was charged to the top of the column and allowed to trickle through. The flow was regulated with a valve at the bottom of column. Temperature was regulated by circulation of 30° C. coolant through the jacket.

Contact time was varied over the range of 0.5 to 1.5 hr. during the course of the reaction in order to evaluate the effect of the conversion level upon selectivity. Samples of reactor effluent were analyzed by gas chromatography to determine the conversion and selectivity to ethylenedioxydipropionitrile. Samples of reactor effluent that had been contacted sufficiently to convert about 97-100% of the starting acrylonitrile showed about 84-88% selectivity to the desired nitriles and about 8-11% high boiling by-products. When conversion was limited, for example to about 82% of the starting acrylonitrile, the product contained about 62% dinitrile and only about 1-2% high-boiling by-products. In addition, 27% mononitrile was produced that could be recycled so that the overall selectivity to nitriles was 98%, based on acrylonitrile converted, at the lower conversion level.

The accompanying Table summarizes the results of the runs made in the manner heretofore described. Listed in the Table are % conversion, % selectivity and analysis of the product and other materials.

TABLE

EFFECT OF CONVERSION ON SELECTIVITY

| Run | Conversion % | Selectivity % | Product Analysis wt. % | | | Other[b] Wt. % |
|---|---|---|---|---|---|---|
| | | | DA[a] | MA[a] | AN[a] | |
| 1 | 100 | 84 | 76.2 | 23.8 | 0 | 11.0 |
| 2 | 99.7 | 88 | 81.9 | 17.9 | 0.2 | 8.1 |
| 3 | 99.7 | 84 | 76.2 | 23.6 | 0.2 | 10.7 |
| 4 | 96.7 | 85 | 71.8 | 26.2 | 2.0 | 10.1 |
| 5 | 95.1 | 92 | 78.0 | 18.9 | 3.1 | 5.6 |
| 6 | 82.3 | 98 | 61.8 | 27.0 | 11.2 | 1.3 |

[a]DA = diadduct; MA = monadduct; AN = acrylonitrile
[b]Other is a polymer of acrylonitrile and can contain unknowns.

Comparison of data for Run 1 with Run 6 indicates that when the conversion as to the cyanoethylation of ethylene glycol decreases from 100% to 82.3% the selectivity increases from 84% to 98%. Further comparison indicates the advantage of lowering conversion, i.e., the amount of unwanted other material dropped from 11 wt.% to 1.3 wt.%.

Use of other labile hydrogen compounds such as methanol, propylene glycol, 1,4-butylene glycol and the like will yield similar results. Also, other catalysts, for example aqueous sodium hydroxide, or other cyanoalkylation reactants can be used with similar results.

Selectivity as used herein equals 100 times the fraction in which the numerator equals the amount of AN in the DA plus the amount of AN in the MA while the denominator equals the amount of AN in the DA plus the amount of AN in the MA plus the other. Thus for Run 1 the % selectivity=

$$100 \times \frac{\frac{53}{115}(23.8) + \frac{106}{168}(76.2)}{\frac{53}{115}(23.8) + \frac{106}{168}(76.2) + 11}$$

=84.3%, which is rounded off to 84%. The number 53 is the molecular weight of CH$_2$CHCN; 115 is the molecular weight for MA; 106 is the molecular weight of two CH$_2$CHCN's and 168 is the molecular weight of the DA.

We claim:

1. In a process for cyanoalkylation of an organic compound having a labile hydrogen atom and selected from the group consisting of monohydric alcohol, polyhydric alcohol, and phenols and wherein the compound is contacted with a cyanoalkene selected from the group consisting of crotononitrile, beta-vinylacrylonitrile and CH$_2$=C(R)CN wherein R is a C$_1$-C$_5$ hydrocarbon radical and the contacting is under cyanoalkylation conditions in a reaction zone and wherein the reaction tends to be accompanied by polymerization of the cyanoalkene with resulting decrease in yield and purity of the desired cyanoalkylation product, the improvement which comprises terminating the reaction when a total of about 60-96% of the cyanoalkene required for complete cyanoalkylation of said compound has been converted to cyanoalkylated products, polymers, and unknowns, whereby the amount of polymers and unknowns is less than that obtained in the cyanoalkylation of said compounds in which the conversion of the cyanoalkene exceeds the above recited upper limit of about 96%, and separating cyanoalkylation product in the reaction product from unreacted cyanoalkene.

2. Process according to claim 1 wherein the cyanoalkylation process is a catalytic cyanoethylation process and the cyanoalkene is acrylonitrile.

3. Process according to claim 2 wherein the cyanoalkylation catalyst is an ion exchange resin.

4. Process according to claim 2 wherein the cyanoalkylation catalyst is aqueous alkali.

5. Process according to claim 4 wherein the cyanoalkylation temperature is maintained in the range between from about 0° C. to about 100° C.

6. Process according to claim 3 wherein the cyanoalkylation selectivity is in excess of about 95%.

7. Process according to claim 1 wherein said organic compound has two labile hydrogen atoms and dinitrile reaction product is separated from unreacted cyanoalkene and from intermediate mononitrile reaction product in the reaction product mixture.

8. Process according to claim 7 wherein the unreacted cyanoalkene and intermediate reaction products are recycled to the reaction zone.

9. Process according to claim 8 wherein the cyanoalkene is acrylonitrile.

10. Process according to claim 9 wherein the temperature in the reaction zone is maintained in the range between from about 0° to about 100° C.

* * * * *